(12) United States Patent
Shikaumi et al.

(10) Patent No.: US 9,282,889 B2
(45) Date of Patent: Mar. 15, 2016

(54) OPHTHALMOLOGIC PHOTOGRAPHING APPARATUS AND CAMERA FOR USE IN OPHTHALMOLOGIC PHOTOGRAPHING

(75) Inventors: Masao Shikaumi, Tokyo (JP); Motoya Takai, Nagareyama (JP); Yasuhiro Nakahara, Kawasaki (JP); Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 132 days.

(21) Appl. No.: 13/392,056

(22) PCT Filed: Aug. 24, 2010

(86) PCT No.: PCT/JP2010/005196
§ 371 (c)(1),
(2), (4) Date: Feb. 23, 2012

(87) PCT Pub. No.: WO2011/024439
PCT Pub. Date: Mar. 3, 2011

(65) Prior Publication Data
US 2012/0147327 A1    Jun. 14, 2012

(30) Foreign Application Priority Data
Aug. 27, 2009    (JP) .................................. 2009-196996

(51) Int. Cl.
*A61B 3/14*    (2006.01)
*G03B 17/48*    (2006.01)

(52) U.S. Cl.
CPC .................. *A61B 3/145* (2013.01); *G03B 17/48* (2013.01)

(58) Field of Classification Search
CPC ............ A61B 3/12; A61B 3/14; A61B 3/0008
USPC .......................................... 351/205, 206, 221
See application file for complete search history.

(56) References Cited

U.S. PATENT DOCUMENTS

| | | | |
|---|---|---|---|
| 6,158,864 A | 12/2000 | Masuda et al. | |
| 2003/0068164 A1 | 4/2003 | Nanjyo | |
| 2005/0041210 A1 | 2/2005 | Isogai et al. | |
| 2006/0203194 A1* | 9/2006 | Suzuki | ............ 351/206 |
| 2009/0046165 A1* | 2/2009 | Kato | ...... H04N 5/232 348/222.1 |
| 2010/0165292 A1* | 7/2010 | Mizuochi | ....... 351/206 |
| 2011/0157550 A1* | 6/2011 | Chen et al. | ..... 351/206 |

(Continued)

FOREIGN PATENT DOCUMENTS

| | | |
|---|---|---|
| CN | 1411782 A | 4/2003 |
| CN | 1539371 A | 10/2004 |
| CN | 101254092 A | 9/2008 |

(Continued)

*Primary Examiner* — Mahidere Sahle
(74) *Attorney, Agent, or Firm* — Canon U.S.A., Inc., IP Division

(57) ABSTRACT

A camera, which is removably mountable on an ophthalmologic photographing apparatus including an illumination optical system configured to illuminate a subject's eye with illumination light, includes an imaging unit configured to form an image from return light from the subject's eye through a photographing optical system in the ophthalmologic photographing apparatus, a development unit configured to develop a moving image or a still image of the subject's eye based on an output signal from the imaging unit with using a development parameter based on a wavelength range of the illumination light, and a display unit configured to display the moving image or the still image developed by the development unit.

32 Claims, 8 Drawing Sheets

(56) References Cited

U.S. PATENT DOCUMENTS

| | | | |
|---|---|---|---|
| 2011/0170063 A1* | 7/2011 | Ooban et al. | 351/206 |
| 2012/0092617 A1* | 4/2012 | Muto et al. | 351/206 |

FOREIGN PATENT DOCUMENTS

| | | | |
|---|---|---|---|
| CN | 201133995 Y | 10/2008 |
| CN | 201166769 Y | 12/2008 |
| EP | 1138255 A | 10/2001 |
| JP | 1119042 A | 1/1999 |
| JP | 2003-325456 A | 11/2003 |
| JP | 2004-229884 A | 8/2004 |
| JP | 2005-270365 A | 10/2005 |
| JP | 2005-278747 A | 10/2005 |
| JP | 2006-006653 A | 1/2006 |
| JP | 2006-061328 A | 3/2006 |
| JP | 2007-151651 A | 6/2007 |
| JP | 2008-119201 A | 5/2008 |
| JP | 4094378 B2 | 6/2008 |
| JP | 2008-212346 A | 9/2008 |
| WO | 2009/092598 A | 7/2009 |

* cited by examiner

OPHTHALMOLOGIC PHOTOGRAPHING APPARATUS AND CAMERA FOR USE IN OPHTHALMOLOGIC PHOTOGRAPHING

TECHNICAL FIELD

The present invention relates to an ophthalmologic photographing apparatus for use in, e.g., ophthalmological clinics, and a camera for use in ophthalmologic photographing.

BACKGROUND ART

For fundus examination, diabetes testing, and other purposes, a fundus camera has been conventionally used. With such a conventional fundus camera, a fundus of an eye is illuminated with visible light or infrared light for positioning and focusing, and an image of the fundus is captured with a flash.

Generally, a single-lens reflex camera is used for still image shooting. To perform monitor observation, however, a monitor imaging device and a display device for displaying an image captured by the monitor imaging device are required in addition to the photographing device.

Japanese Patent No. 4,094,378 discusses a portable ophthalmologic apparatus capable of photographing by attaching a camera-equipped mobile phone or a compact digital camera which can perform photographing outside an examination room.

The portable ophthalmologic apparatus discussed in Japanese Patent No. 4,094,378 is predicated on the use of a mobile phone or a compact digital camera and provides lower image quality than a digital single-lens reflex camera which includes an image sensor of greater size.

However, in a case where a single-lens reflex camera is employed, a monitor imaging device and a monitor display device need to be individually provided, which cause an increase in cost and in apparatus size.

CITATION LIST

Patent Literature

PTL 1: Japanese Patent No. 4,094,378

SUMMARY OF INVENTION

According to an aspect of the present invention, a camera which is removably mountable on an ophthalmologic photographing apparatus including an illumination optical system configured to illuminate a subject's eye with illumination light includes an imaging unit configured to form an image from return light from the subject's eye through a photographing optical system in the ophthalmologic photographing apparatus, a development unit configured to develop a moving image or a still image of the subject's eye based on an output signal from the imaging unit with using a development parameter based on a wavelength range of the illumination light, and a display unit configured to display the moving image or the still image developed by the development unit.

According to another aspect of the present invention, an ophthalmologic photographing apparatus on which a camera is removably mountable, wherein the camera includes an imaging unit configured to capture an image of a subject's eye and a display unit configured to display the image of the subject's eye includes a photographing optical system configured to form, on the imaging unit of the camera, an image from return light from the subject's eye illuminated with light through an illumination optical system, a setting unit configured to set a development parameter based on a wavelength range of the light illuminating the subject's eye, a live view unit configured to cause the display unit to display a moving image of the subject's eye based on an output signal from the imaging unit and on the development parameter, and a transmission unit configured to transmit to the camera either a signal for displaying the moving image of the subject's eye in monochrome when the wavelength range is in an infrared region or a signal for displaying a still image of the subject's eye in color when the wavelength range is in a visible region.

According to yet another aspect of the present invention, a camera which is removably mountable on an ophthalmologic photographing apparatus including an illumination optical system configured to illuminate a subject's eye with illumination light includes an imaging unit configured to form an image from return light from the subject's eye through a photographing optical system in the ophthalmologic photographing apparatus, and a reception unit configured to receive, from the ophthalmologic photographing apparatus, either a still image photographing signal obtained by forming an image on the imaging unit from visible light from the subject's eye or a moving image observation signal obtained by forming an image on the imaging unit from infrared light from the subject's eye.

Advantageous Effects of Invention

The ophthalmologic photographing apparatus and the camera for use in ophthalmologic photographing according to the present invention are provided with a digital single-lens reflex camera. This enables the ophthalmologic photographing apparatus and the camera to have a smaller size and to provide higher quality images than a fundus camera using a camera-equipped mobile phone or a compact digital camera. Further features and aspects of the present invention will become apparent from the
following detailed description of exemplary embodiments with reference to the attached drawings.

BRIEF DESCRIPTION OF DRAWINGS

The accompanying drawings, which are incorporated in and constitute a part of the specification, illustrate exemplary embodiments, features, and aspects of the invention and, together with the description, serve to explain the principles of the invention.

DESCRIPTION OF EMBODIMENTS

Various exemplary embodiments, features, and aspects of the invention will be described in detail below with reference to the drawings.

Figure 1:
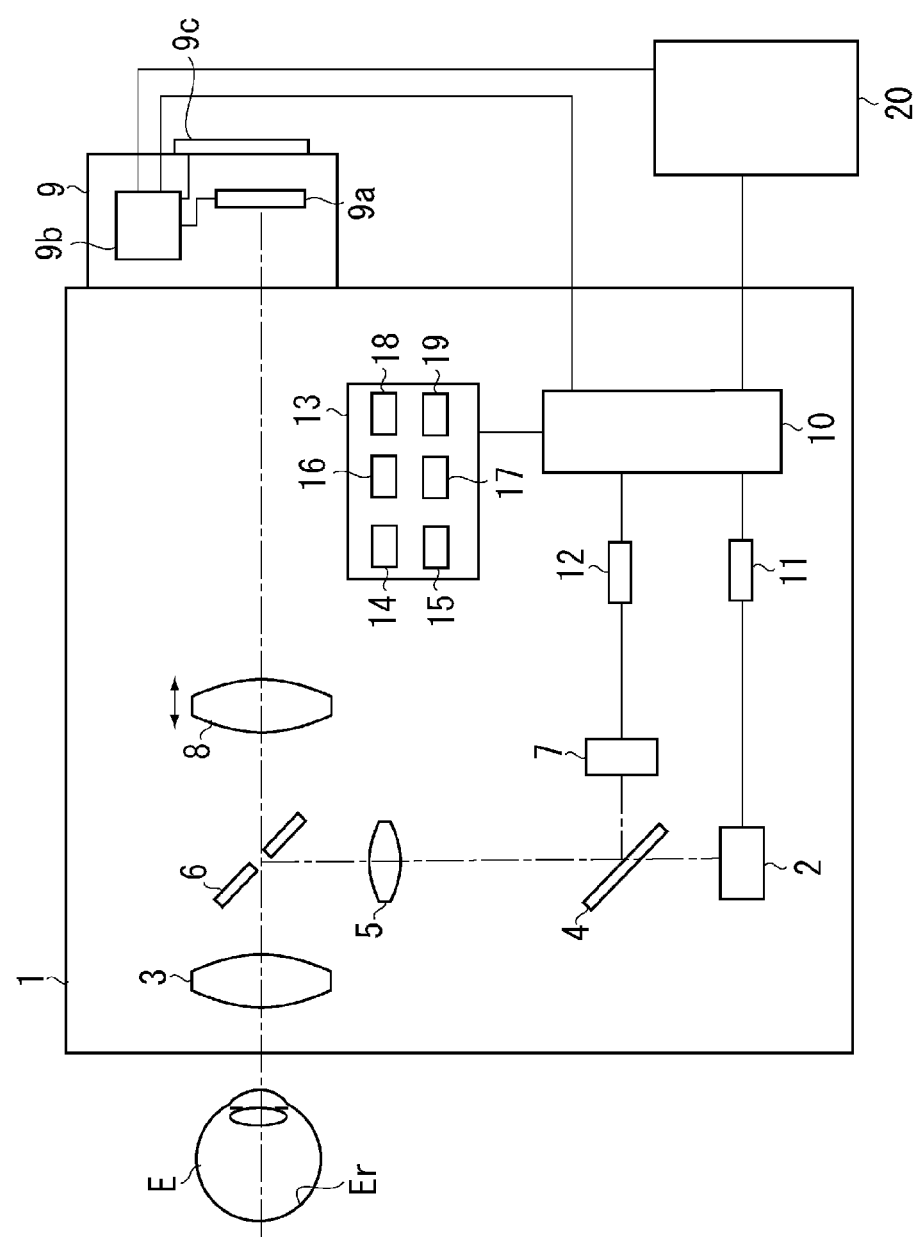
FIG. 1 illustrates a structure of a fundus camera according to a first exemplary embodiment.

FIG. 1 illustrates a structure of a fundus camera according to a first exemplary embodiment which is used as an ophthalmologic photographing apparatus. A fundus camera body 1 placed in front of a subject's eye E includes an observation illumination optical system from an observation light source 2 to an objective lens 3. The observation light source 2 includes a halogen lamp, for example. The objective lens 3 is placed to face the subject's eye E. The observation illumination optical system includes the observation light source 2, a dichroic minor 4, a relay lens 5, and a perforated mirror 6 arranged in that order. The fundus camera body 1 also includes a photographic light source 7 as a photographing illumination optical system disposed in an incident direction of the dichroic mirror 4. The photographic light source 7 includes a xenon lamp.

A focusing lens 8 as a photographing optical system is disposed behind the perforated minor 6. The focusing lens 8 moves in a direction of an optical axis to adjust focus. A digital single-lens reflex camera 9 is removably attached on the fundus camera body 1 that is located on an extension of the optical axis of the focusing lens 8.

The digital single-lens reflex camera 9 includes an image sensor 9a which converts a formed optical image into an electrical signal. An output of the image sensor 9a is connected to a control unit 9b in the digital single-lens reflex camera 9. On the back of the digital single-lens reflex camera 9, a liquid crystal display 9c serving as a display unit is provided. The liquid crystal display 9c is connected to the output of the control unit 9b.

The fundus camera body 1 further includes a control circuit 10. Outputs of the control circuit 10 are connected to the observation light source 2 and to the photographic light source 7 via driving circuits 11 and 12, respectively. The control circuit 10 is also connected to the control unit 9b in the digital single-lens reflex camera 9 and to a switch board 13 in the fundus camera body 1. The switch board 13 is provided with a photographing mode changing switch 14, a fixation lamp position changing switch 15, a left and right eye detection switch 16, a small pupil diameter photographing switch 17, a zooming switch 18, and a release switch 19.

A computer 20 is externally provided to the fundus camera body 1 and is connected to the control unit 9b in the digital single-lens reflex camera 9 and to the control circuit 10 in the fundus camera body 1 via a universal serial bus (USB) and/or a serial port.

The photographing mode changing switch 14 is used to switch among a plurality of photographing modes of the fundus camera. Those photographing modes include a color photographing mode in which color images are captured, a fundus autofluorescence photographing mode in which autofluorescence of lipofuscin, which is waste material accumulating in the fundus of the eye, is captured, and a fluorescence photographing mode in which fluorescence of intravenous fluorescein is captured. The photographing modes also include a red free mode and a cobalt mode in which blood vessel conditions are easily identifiable.

To achieve a required spectrum in each photographing mode, an optical filter (not shown) is inserted to or removed from the illumination optical system and the photographing optical system.

The fixation lamp position changing switch 15 is used to change a lighting position of an internal fixation lamp to guide a line of sight of the subject's eye and to change a photographing range on the fundus Er.

The left and right eye detection switch 16 is used to detect whether the left or right eye of the subject is being photographed. The left or right eye is detected from a relative relationship between a position of the subject's face and an imaging optical axis of the fundus camera body 1.

For a subject's eye E whose pupil diameter is small, the small pupil diameter photographing switch 17 is used to perform switching between baffles and between optical systems, which are not shown, to reduce image vignetting.

The zooming switch 18 is used to photograph an enlarged image. Upon selection of enlarged-image photographing, a photographed image is magnified twice by trimming and digital-zooming. Zoom photographing can also be performed by inserting or removing an optical system (not shown) to or from a photographic optical path or by moving a variable focus optical system in the direction of the optical axis to change a focal length of the optical system.

In response to pressing of the release switch 19, the control circuit 10 transmits a release signal to the control unit 9b in the digital single-lens reflex camera 9. Transmission of the release signal causes the digital single-lens reflex camera 9 to perform photographing. Recently, there has been an increasing number of models of digital single-lens reflex cameras which have a live view function as a live view unit. The live view is a function in which, with the shutter opened by retracting a quick-return minor included in the digital single-lens reflex camera 9, an image formed on the image sensor 9a is successively read to continuously display the image on the liquid crystal display 9c on the back.

In the present exemplary embodiment, upon operation of any switch of the switch board 13, the control circuit 10 transmits a switch condition to the computer 20 via a serial port or a USB. The computer 20 generates an information display image according to the condition of the fundus camera body 1, and transmits the information display image to the control unit 9b in the digital single-lens reflex camera 9 via the serial port or the USB. The control unit 9b superimposes the information display image transmitted from the computer 20 on a live view image displayed on the liquid crystal display 9c, to display the resultant image.

Figure 2:
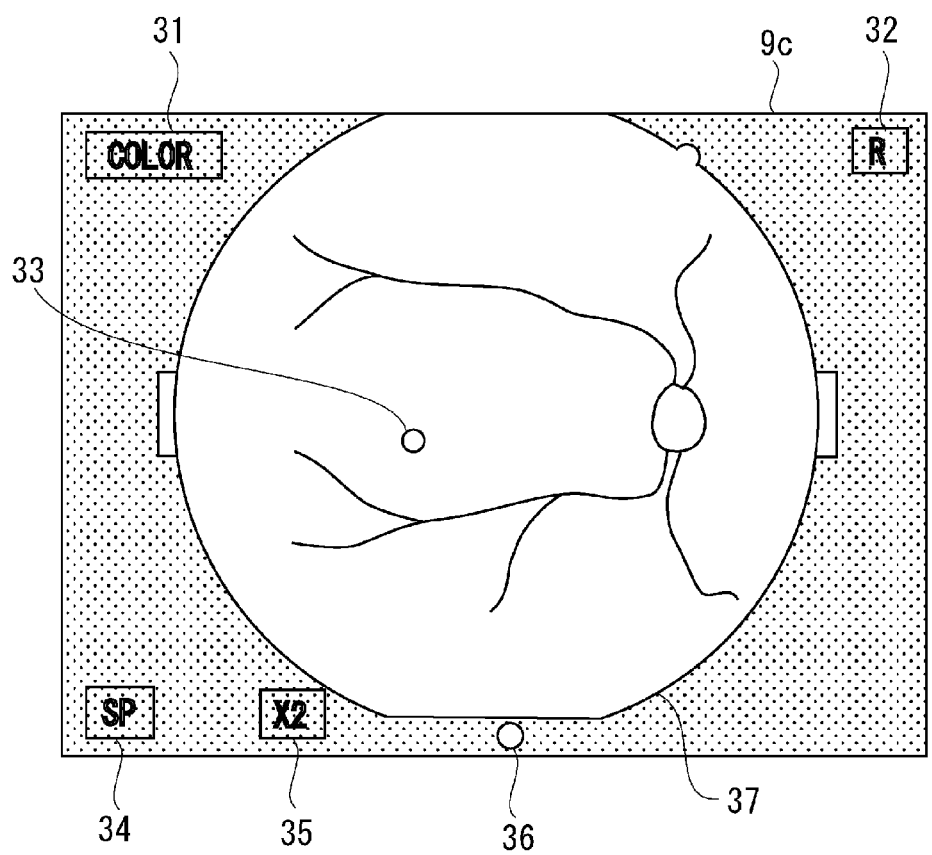
FIG. 2 illustrates an information display.

FIG. 2 illustrates an example of an information display displayed on the liquid crystal display 9c of the digital single-lens reflex camera 9 when a user operates the fundus camera. On a photographed fundus image, a photographing mode display field 31, a right eye/left eye information field 32, a fixation lamp display position 33, a small pupil diameter photographing display field 34, a digital zooming display field 35, a ready-for-photographing display field 36, and an electronic mask 37 for cutting a flare in a peripheral portion of the fundus image are displayed.

FIG. 2 illustrates a screen in the color photographing mode. In this mode, "COLOR" appears in the photographing mode display field 31 in an upper left corner of the screen. In the other modes, "FAF (indicating the fundus auto-fluorescence photographing mode)", "FA (indicating the fluorescence photographing mode)", "RED FREE (indicating the red free mode)", and "COBALT (indicating the cobalt mode)" appear. Any photographing modes other than those described above may also be displayed on the liquid crystal display 9c.

In the right eye/left eye information field 32, "R" appears in the case of the right eye, and "L" in the case of the left eye. The fixation lamp display position 33 appears in a location where the internal fixation lamp is illuminating. In the small pupil diameter photographing display field 34, "SP (small pupil)" is indicated when small pupil diameter photographing is designated. In the digital zooming display field 35, "×2 (two-fold magnification)" is indicated upon selection of enlarged-image photographing with zooming function. The ready-for-photographing display field 36 lights up when the fundus camera body 1 completes preparations for photographing, such as completion of flash charging.

Figure 3:
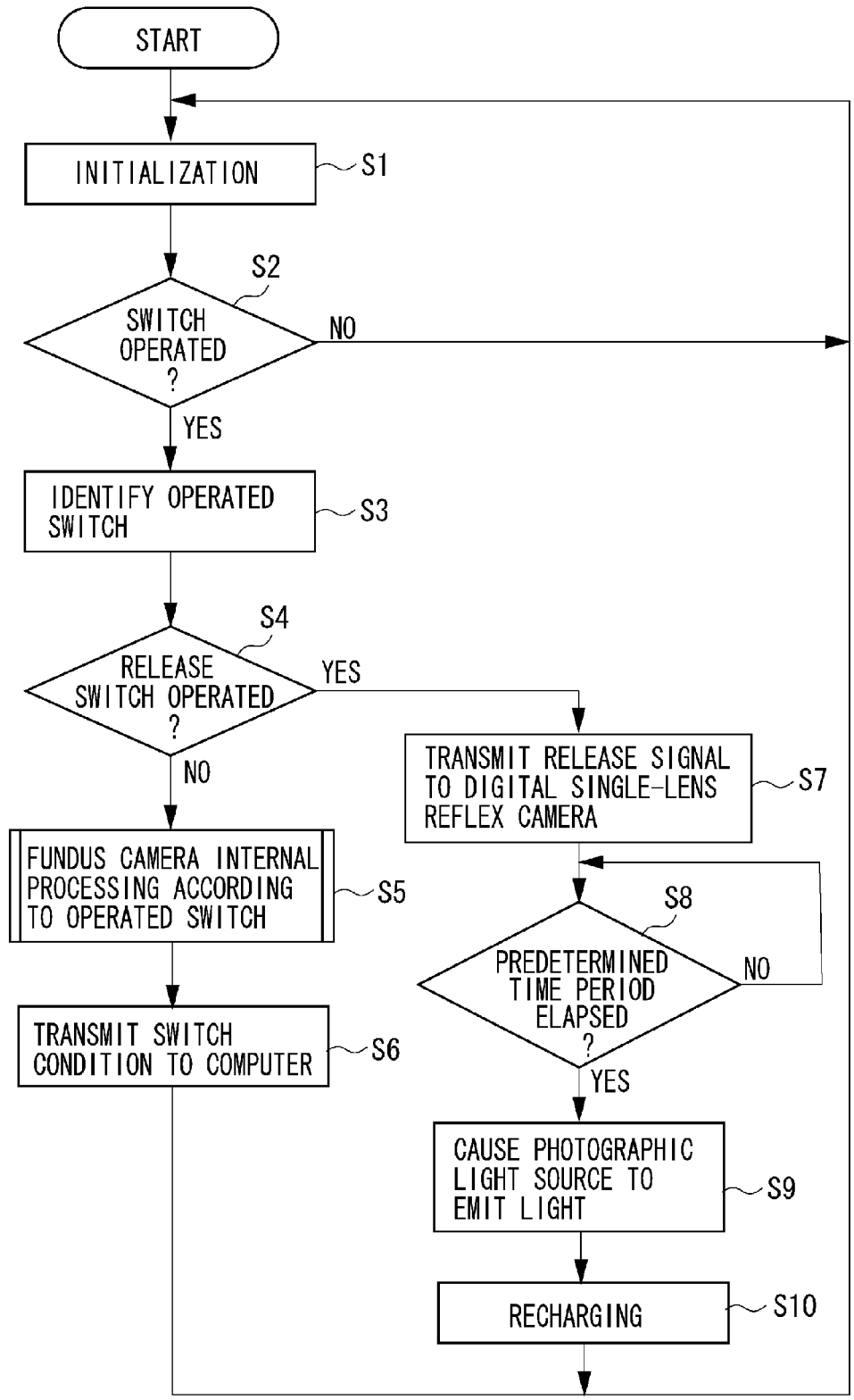
FIG. 3 is a flow chart illustrating an operation of the fundus camera.

FIG. 3 is a flow chart illustrating an operation of the fundus camera body 1. First, when a user turns on the power to start the operation, in step S1, the fundus camera body 1 initializes the internal state thereof. Then, in step S2, the fundus camera body 1 waits for operation of a switch of the switch board 13. The fundus camera body 1 repeats step S2 until the switch is operated. Upon operation of the switch (YES in step S2), the operation proceeds to step S3 and the fundus camera body 1 identifies the operated switch.

Next, in step S4, the fundus camera body 1 determines whether the operated switch is the release switch 19. If the fundus camera body 1 determines that the operated switch is not the release switch 19 (NO in step S4), the operation proceeds to step S5. In step S5, the fundus camera body 1 performs internal processing according to the operated switch. Then, in step S6, the fundus camera body 1 transmits a switch condition to the computer 20, and the operation returns to step S2.

If, in step S4, the fundus camera body 1 determines that the operated switch is the release switch 19 (YES in step S4), then the operation proceeds to step S7. In step S7, the fundus camera body 1 transmits a release signal to the control unit 9b in the digital single-lens reflex camera 9. Next, in step S8, the fundus camera body 1 waits for a pre-determined period of time to elapse, to match the timing when the shutter is opened for the photographing operation of the digital single-lens reflex camera 9 to the timing when the photographic light source 7 emits light. When the predetermined period of time has elapsed (YES in step S8), the operation proceeds to step S9. In step S9, the fundus camera body 1 causes the photographic light source 7 to emit light for photographing. In step S10, the fundus camera body 1 recharges the flash of the photographic light source 7, and the operation returns to step S2.

Figure 4:
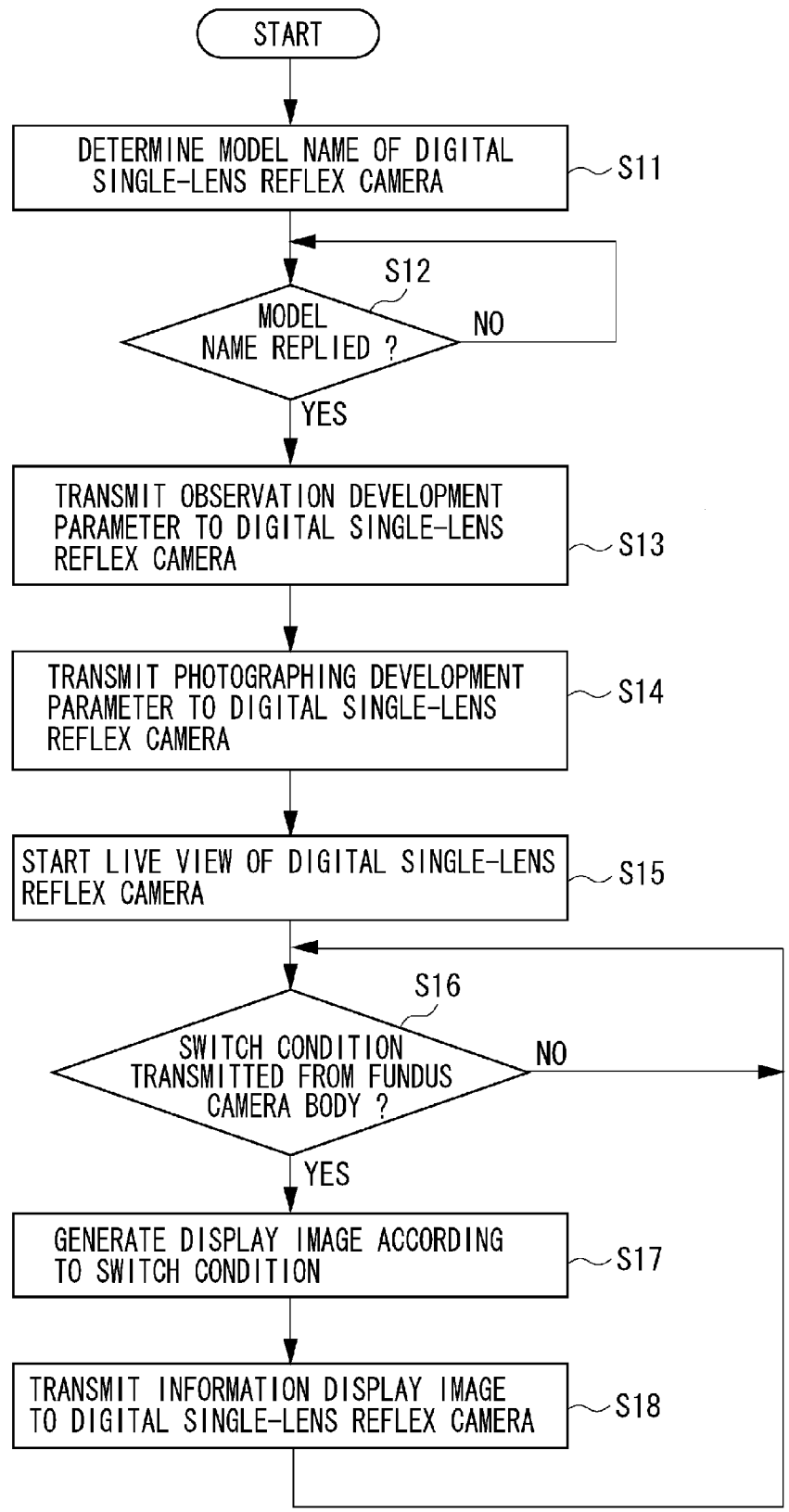
FIG. 4 is a flow chart illustrating an operation of a computer.

FIG. 4 is a flow chart illustrating an operation of the computer 20. When a user turns on the power to the computer 20, in step S11, the computer 20 determines a model name of the digital single-lens reflex camera 9 via a model determination unit (not shown). This is because characteristics of the image sensor 9a employed and the spectral characteristics of a color filter put on the surface of the image sensor 9a vary depending on the model of the digital single-lens reflex camera 9. The computer 20 has stored in advance an observation development parameter and a photographing development parameter for image formation for each model of the connectable digital single-lens reflex camera 9.

In step S12, the computer 20 waits for a reply to the inquiry about the model name. If the reply is provided (YES is step S 12), the operation proceeds to step S13. In step S13, the observation development parameter corresponding to the model name obtained in step S12 is read from the computer 20, and transmitted to the digital single-lens reflex camera 9. The observation development parameter is set in the digital single-lens reflex camera 9.

Next, in step S14, as in step S13, the photographing development parameter corresponding to the model name is read from the computer 20, and transmitted to the digital single-lens reflex camera 9. The photographing development parameter is set in the digital single-lens reflex camera 9.

The observation light source 2 which is a halogen lamp and the photographic light source 7 which is a xenon lamp are different types of light sources. Nevertheless, the change of the development parameters in steps S13 and S14 enables optimum observation and photographing for the light sources 2 and 7.

Subsequently, in step S15, the computer 20 starts live view of the digital single-lens reflex camera 9. Then, the operation proceeds to step S16. In step S16, the computer 20 waits for the switch condition to be transmitted from the fundus camera body 1 in above described step S6. The computer 20 repeats step S16 until the switch condition is transmitted. If the switch condition is transmitted (YES in step S16), the operation proceeds to step S17. In step S17, the computer 20 displays information display contents such as shown in FIG. 2 according to the switch condition transmitted from the fundus camera body 1.

In step S18, the computer 20 transmits the display image generated in step S17 to the digital single-lens reflex camera 9. Then, the operation returns to step S16 to repeat steps S16 to S18.

Figure 5:
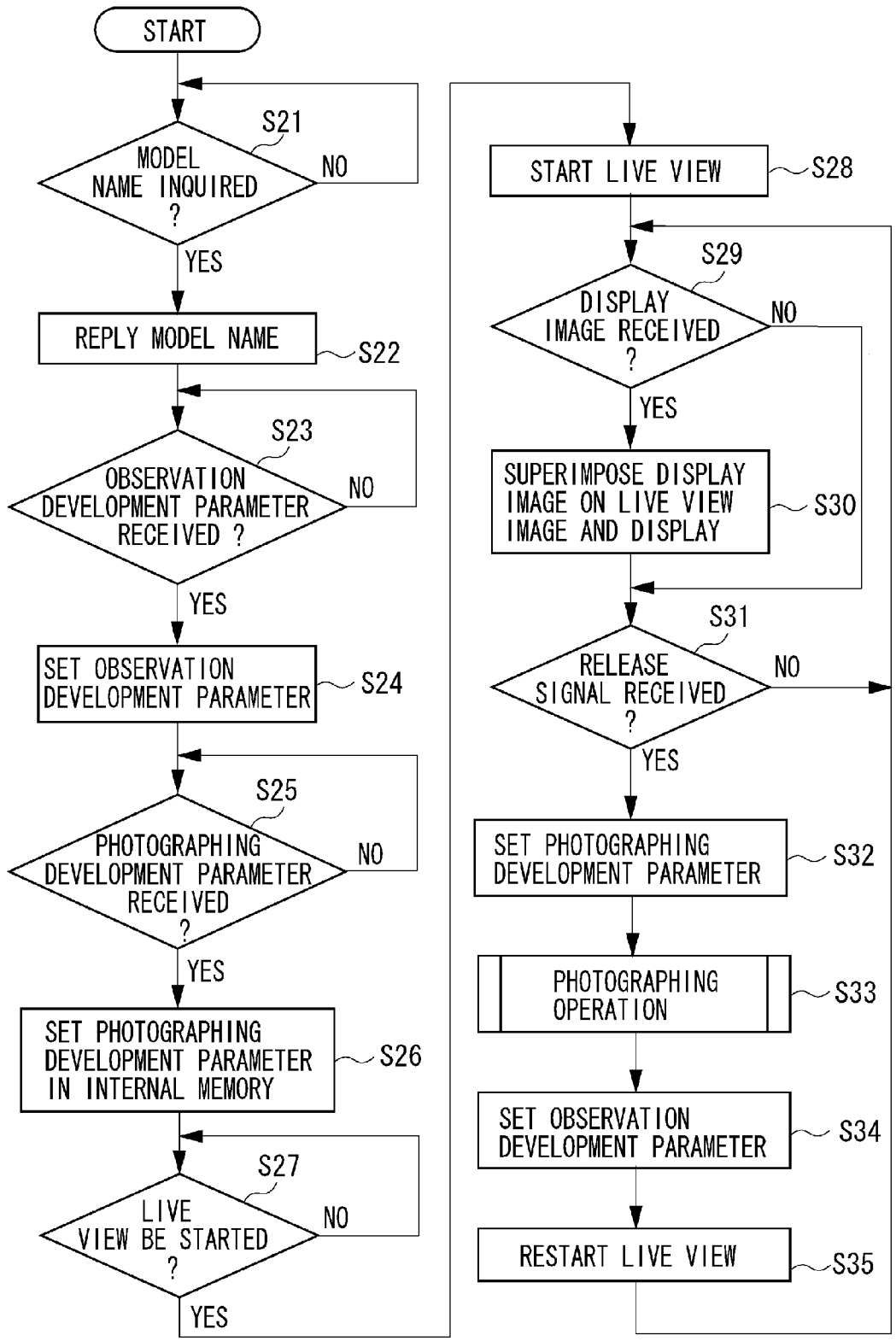
FIG. 5 is a flow chart illustrating an operation of a digital single-lens reflex camera.

FIG. 5 is a flow chart illustrating an operation of the digital single-lens reflex camera 9. When a user turns on the power, in step S21, the digital single-lens reflex camera 9 waits for an inquiry about the model name transmitted from the computer 20 in above described step S11 in FIG. 4. If there is an inquiry about the model name, the operation proceeds to step S22 and the digital single-lens reflex camera 9 provides the model name as a reply.

Next, in step S23, the digital single-lens reflex camera 9 waits to receive the observation development parameter corresponding to the model thereof from the computer 20. Upon receiving the observation development parameter (YES in step S23), in step S24, the digital single-lens reflex camera 9 sets the observation development parameter in a memory in the control unit 9b.

Then, in step S25, the digital single-lens reflex camera 9 waits to receive the photographing development parameter corresponding to the model thereof from the computer 20. Upon receiving the photographing development parameter (YES in step S25), in step S26, the digital single-lens reflex camera 9 sets the photographing development parameter in the memory in the control unit 9b.

The operation then proceeds to step S27 and the digital single-lens reflex camera 9 waits to receive an instruction to start live view provided from the computer 20 in step S15 in FIG. 4. Upon receipt of the instruction (YES in step S27), in step S28, a live view operation is started, and the digital single-lens reflex camera 9 is used as an observation unit. More specifically, the observation light source 2 is caused to emit light, and the quick return mirror in the digital single-lens reflex camera 9 is retracted to open the shutter. A fundus image formed on the image sensor 9a is successively read, and developed using the observation development parameter to display the image on the liquid crystal display 9c. This operation is continued while the live view is performed.

The operation then proceeds to step S29 and it is determined whether the digital single-lens reflex camera 9 has received a display image from the computer 20 in step S18 in FIG. 4. If the digital single-lens reflex camera 9 has received the transmitted display image (YES in step S29), then the operation proceeds to step S30. In step S30, the digital single-lens reflex camera 9 superimposes the transmitted display image on a live view image to display the resultant image on the liquid crystal display 9c. The operation then proceeds to step S31.

If the digital single-lens reflex camera 9 has not received the display image in step S29 (No in step S29), the operation proceeds to step S31. In step S31, it is determined whether the digital single-lens reflex camera 9 has received a release signal transmitted from the fundus camera body 1 in step S7 in FIG. 3. The release signal serves as condition identification means. In step S31, if the digital single-lens reflex camera 9 has not received the release signal (NO in step S31), the operation returns to step S29 to repeat steps S29 to S31. If the digital single-lens reflex camera 9 has received the release signal (YES in step S31), the operation proceeds to step S32. In step S32, the digital single-lens reflex camera 9 sets, as the development parameter, the photographing development parameter set in the memory in the control unit 9b, using a parameter changing unit.

The operation then proceeds to step S33 and the digital single-lens reflex camera 9 starts still image photographing to accumulate data for a still image on the image sensor 9a for a given period of time. In the accumulation process, the photographic light source 7 emits light for photographing in step S9 in FIG. 3. The still image is then read and developed using the photographing development parameter. The developed still image is recorded on a storage medium (not shown) in the digital single-lens reflex camera 9. Alternatively, the still image may be transmitted to the connected computer 20.

When the still image photographing is terminated, the operation proceeds to step S34. In step S34, the digital single-lens reflex camera 9 sets the observation development parameter again as the development parameter. In step S35, the digital single-lens reflex camera 9 restarts live view. Then, the operation returns to step S29.

Figure 6:
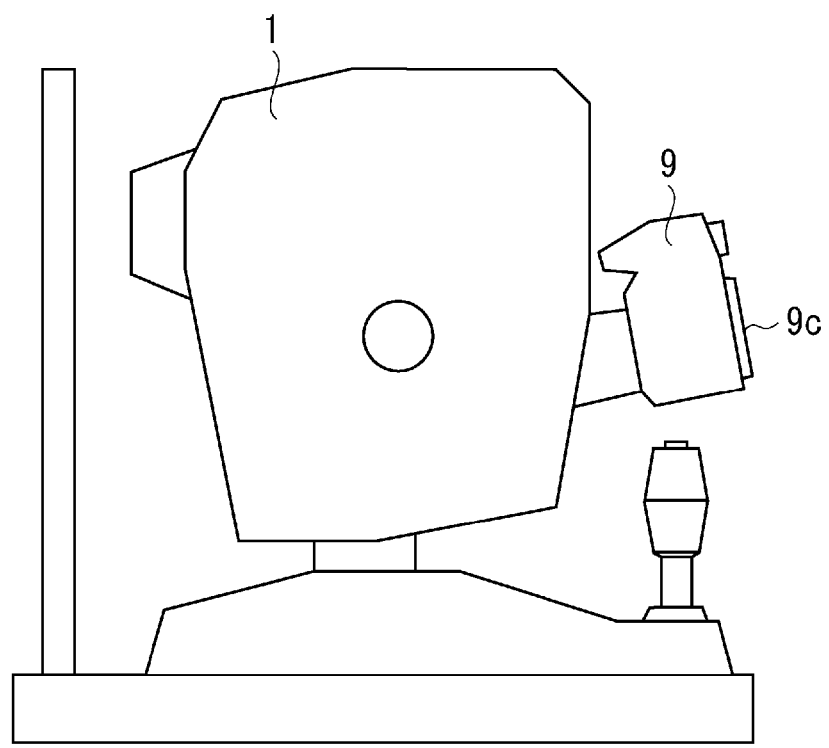
FIG. 6 is a side view illustrating a fundus camera with a digital single-lens reflex camera attached thereto.

FIG. 6 is a side view illustrating the fundus camera body 1 with the digital single-lens reflex camera 9 attached thereon. It is desired in term of viewing angle that the liquid crystal display 9c may be located approximately in front of an examiner because images are displayed on the liquid crystal display 9c on the back of the digital single-lens reflex camera 9. In the case of a structure in which the digital single-lens reflex camera 9 is placed on a part of the fundus camera body 1 that is located slightly lower than a position straight in front of the examiner, the liquid crystal display 9c may be upwardly inclined at an angle of about 10 degrees with respect to a vertical direction.

As set forth above, in the present exemplary embodiment, the live view function of the digital single-lens reflex camera 9 is used to display images during observation. This configuration eliminates the need to provide an image senor and a display device separately from the digital single-lens reflex camera 9. Further, color variation, e.g., occurring due to the use of the different light sources in observation and in photographing can be accommodated by the use of different development parameters for observation and for photographing.

For a display image, it is not necessary to transmit information for the entire screens each time. The computer 20 may generate only an image for a portion of the display that is to be changed, and transmit the generated partial image and the coordinate values representing the partial image to the digital single-lens reflex camera 9.

In the present exemplary embodiment, it is described the case in which different development parameters are set for observation and for still image photographing. However, the development parameter may be further changed according to a size of an image to be recorded, for example. In that case, it is possible to set a development parameter according to the resolution. Moreover, some models of digital single-lens reflex cameras recently available on the market are capable of recording a moving image. In such models, a development parameter different from those set for observation and for still image photographing may be set for moving image recording.

In the first exemplary embodiment, it is described that the computer 20 generates a display image according to a switch change in the switch board 13 in the fundus camera body 1. In a second exemplary embodiment, a switch change is transmitted to a digital single-lens reflex camera 9 as status data composed of characters or symbol data. The digital single-lens reflex camera 9 generates a display image corresponding to the transmitted status data. The structure of a fundus camera according to the present exemplary embodiment is the same as that of the first exemplary embodiment.

Figure 7:
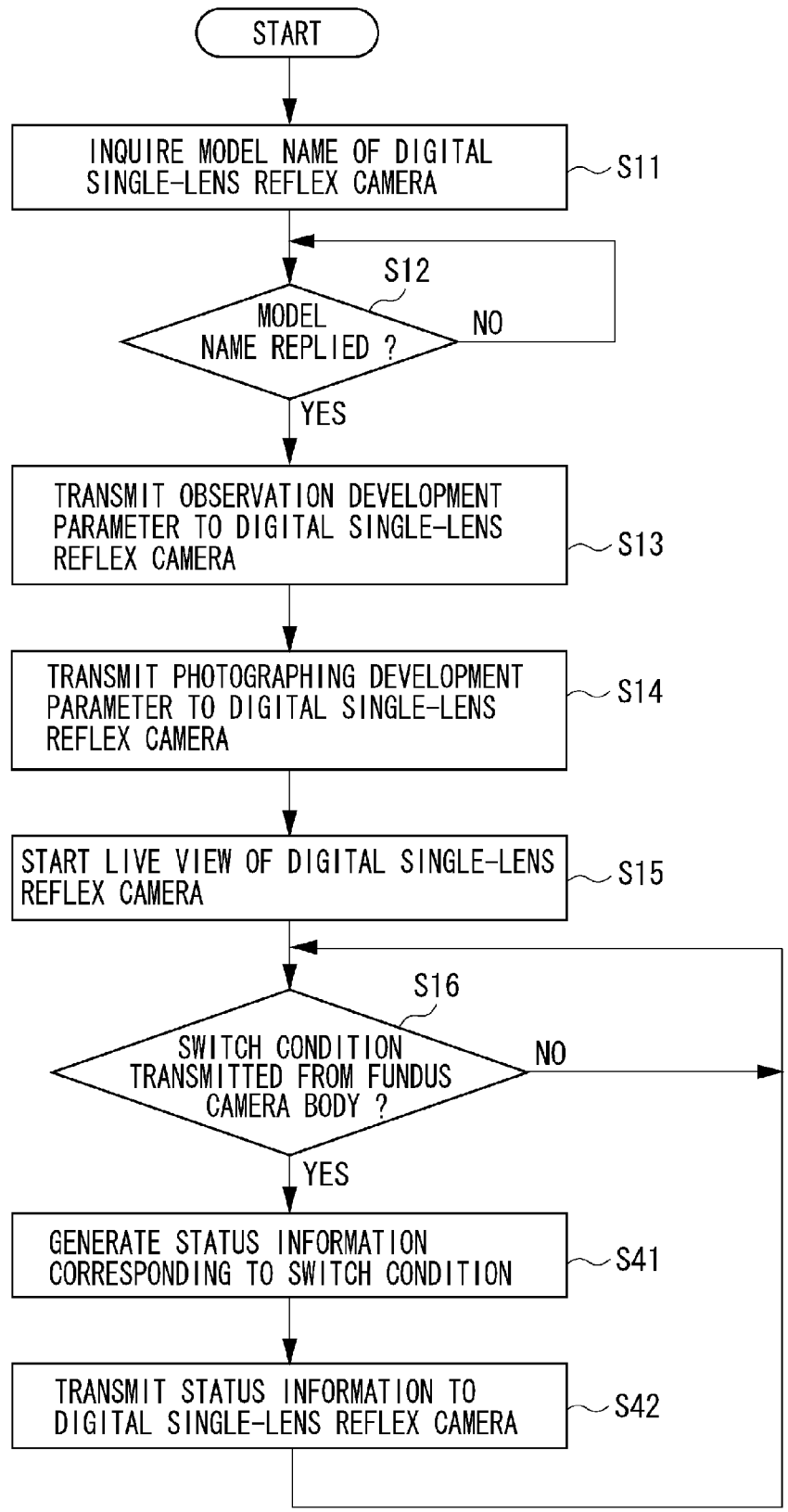
FIG. 7 is a flow chart illustrating an operation of a computer according to a second exemplary embodiment.

FIG. 7 is a flow chart illustrating an operation of a computer 20 according to the second exemplary embodiment. The same operations as those in FIG. 4 in the first exemplary embodiment are identified by the same step numbers, and the description thereof will be omitted herein.

In the second exemplary embodiment, in step S16, if the fundus camera body 1 transmits a switch condition (YES in step S16), then in step S41, the computer 20 generates status information corresponding to the switch condition. Examples of the status information are as flows. In the case of small pupil diameter photographing or zoom photographing, for example, the computer 20 sets bits corresponding to a status variable ranging from 1 to 2 bytes. In the case of photographing mode, the computer 20 generates a character string, such as "mode: COLOR". In step S42, the computer 20 transmits the status information generated in step S41 to the digital single-lens reflex camera 9.

Figure 8:
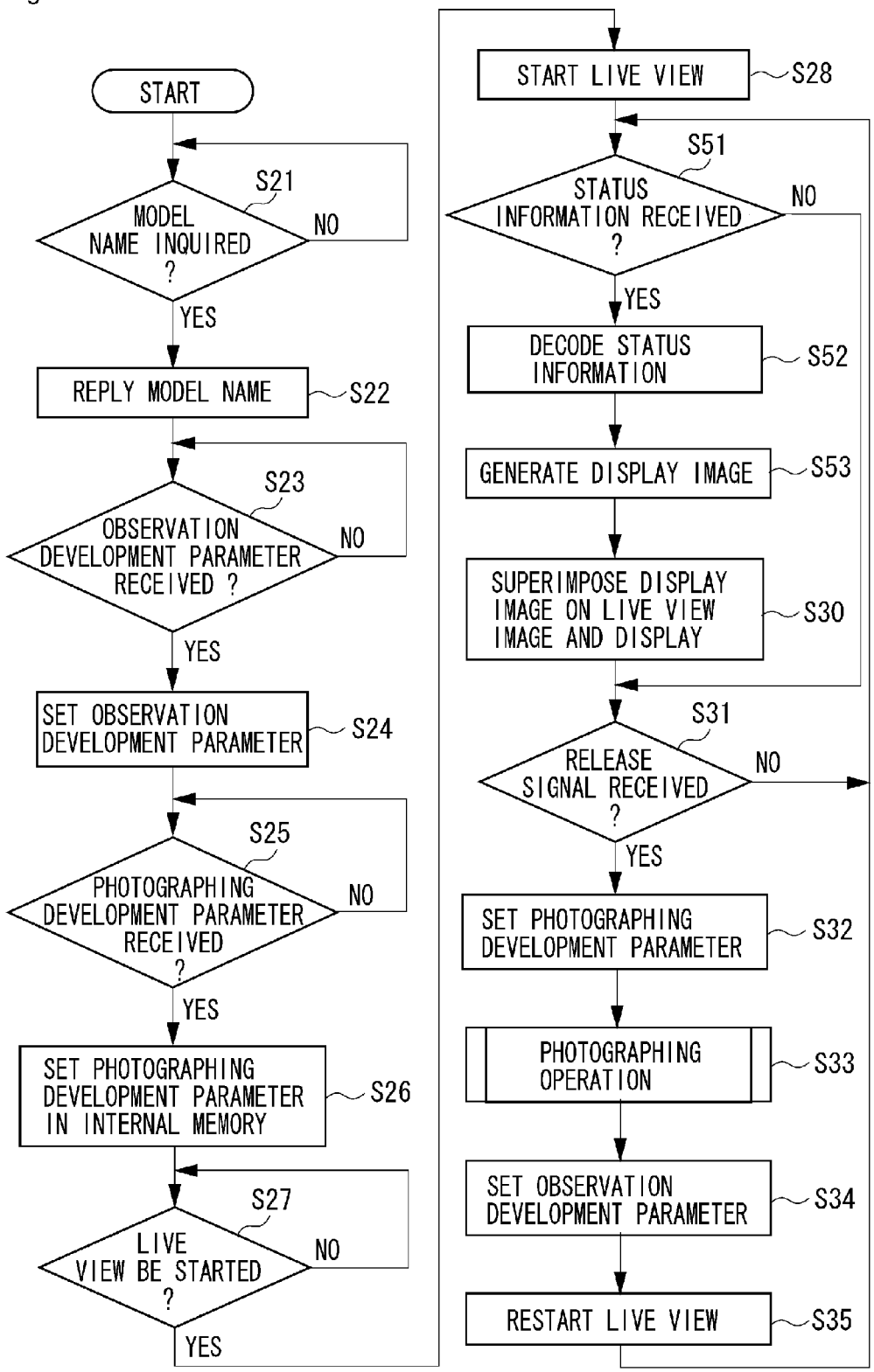
FIG. 8 is a flow chart illustrating an operation of a digital single-lens reflex camera.

FIG. 8 is a flow chart illustrating an operation of the digital single-lens reflex camera 9 according to the second exemplary embodiment. The same operations as those in FIG. 5 in the first exemplary embodiment are identified by the same step numbers, and the description thereof will be omitted herein.

After the digital single-lens reflex camera 9 starts live view in step S28, it is determined in step S51 whether the digital single-lens reflex camera 9 has received status information from the computer 20. If the digital single-lens reflex camera 9 has not received the status information (NO in step S51), the operation proceeds to step S31. In step S31, it is determined whether the digital single-lens reflex camera 9 has received a release signal.

If the digital single-lens reflex camera 9 has received the status information (YES in step S51), then in step S52, the digital single-lens reflex camera 9 decodes the status information. In step S53, the digital single-lens reflex camera 9 generates a display image based on the result of the decoding. Then, in step S30, the digital single-lens reflex camera 9 superimposes the generated display image on a live view image to display the resultant image.

In the second exemplary embodiment, since no image data is transmitted, an amount of communication traffic is reduced, so that display responsibility to a switch operation can be increased.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-196996 filed Aug. 27, 2009, which is hereby incorporated by reference herein in its entirety.

The invention claimed is:

1. A camera which is detachable from a fundus camera body including an illumination optical system configured to illuminate a subject's eye with illumination light and a photographing optical system configured to photograph the subject's eye illuminated by the illumination optical system with one of visible light and infrared light, the camera comprising:
    an image sensor including a light receiving surface to receive return light from the subject's eye through the photographing optical system; and
    a display unit configured to display an image of the subject's eye formed on the light receiving surface in monochrome based on an output signal from the image sensor in a case where the illumination optical system illuminates the subject's eye with the infrared light, and to display an image of the subject's eye formed on the light receiving surface in color based on an output signal from the image sensor in a case where the illumination optical system illuminates the subject's eye with visible light.

2. The camera according to claim 1, further comprising:
    a developing unit configured to develop an output signal read from the image sensor for observation in a case where the illumination optical system illuminates the subject's eye with the infrared light,
    wherein the display unit displays a monochrome moving image of the subject's eye obtained by developing the output signal for observation.

3. The camera according to claim 1, wherein when the wavelength range of the illumination light is in a visible region, the still image of the subject's eye is displayed in color.

4. The camera according to claim 1, further comprising:
    a reflective member removable from an optical path; and
    a control unit configured to remove the reflective member from the optical path so that a shutter is opened in a case where the illumination optical system illuminates the subject's eye with the infrared light.

5. The camera according to claim 1, further comprising a display control unit configured to cause the display unit to display information about the ophthalmologic photographing apparatus,
    wherein the display control unit receives display contents of the information about the ophthalmologic photographing apparatus as image data, and superimposes the image data on the moving image or the still image to display a resultant image, or receives display contents of the information about the ophthalmologic photographing apparatus as characters or symbol data, and decodes the characters or the symbol data to display decoded data as an image.

6. An ophthalmologic photographing apparatus comprising a fundus camera body including an illumination optical system configured to illuminate a subject's eye and a photographing optical system configured to photograph the subject's eye illuminated by the illumination optical system with one of infrared light and visible light, and a camera detachable from the fundus camera body and including an image sensor with a light-receiving surface to receive return light from the subject's eye through the photographing optical system and a display unit, the ophthalmologic photographing apparatus comprising:
    a first display control unit configured to cause the display unit to display an image of the subject's eye formed on the light-receiving surface in monochrome based on an output signal from the image sensor in a case where the illumination optical system illuminates the subject's eye with the infrared light; and
    a second display control unit configured to cause the display unit to display an image of the subject's eye formed on the light-receiving surface in color based on an output signal from the image sensor in a case where the illumination optical system illuminates the subject's eye with the visible light.

7. The ophthalmologic photographing apparatus according to claim 6, wherein the fundus camera body includes an attaching unit configured to attach the camera so that the display unit is upwardly inclined at a predetermined degree.

8. A camera which is detachable from an ophthalmologic photographing apparatus including an illumination optical system configured to illuminate a subject's eye with illumination light, the camera comprising:
    an image sensor configured to form an image from return light from the subject's eye through a photographing optical system in the ophthalmologic photographing apparatus; and
    a reception unit configured to receive, from the ophthalmologic photographing apparatus, either a still image photographing signal obtained by forming an image on the image sensor from visible light from the subject's eye or a moving image observation signal obtained by forming an image on the image sensor from infrared light from the subject's eye.

9. The camera according to claim 1, wherein, in a case where an auto-fluorescence photographing mode is selected from a plurality of photographing modes including a color photographing mode and the auto-fluorescence photographing mode, the display unit displays an auto-fluorescence photographed image of the subject's eye and a display form indicating the auto-fluorescence photographing mode.

10. The ophthalmologic photographing apparatus according to claim 6, further comprising:
    a photographing mode selection unit configured to select one of a plurality of photographing modes including a color photographing mode and an auto-fluorescence photographing mode;
    a generation unit configured to generate a display form indicating the auto-fluorescence photographing mode in a case where the photographing mode selection unit selects the auto-fluorescence photographing mode; and
    a third display control unit configured to cause the display unit to display an auto-fluorescence photographed image of the subject's eye and the display form.

11. The ophthalmologic photographing apparatus according to claim 6, further comprising:
    a developing unit configured to develop an output signal read from the image sensor for observation in a case where the illumination optical system illuminates the subject's eye with the infrared light,
    wherein the first display control unit causes the display unit to display a monochrome moving image of the subject's eye obtained by developing the output signal for observation.

12. The ophthalmologic photographing apparatus according to claim 6, further comprising:
    a removing control unit configured to remove a reflective member disposed in the camera from an optical path so that a shutter of the camera is opened in a case where the illumination optical system illuminates the subject's eye with the infrared light.

13. An ophthalmologic system comprising:
   an ophthalmologic photographing apparatus including an illumination optical system configured to illuminate a subject's eye and a photographing optical system configured to photograph the subject's eye illuminated by the illumination optical system with one of infrared light and visible light;
   a camera detachable from the ophthalmologic photographing apparatus and including an image sensor with a light-receiving surface to receive return light from the subject's eye through the photographing optical system and a display unit;
   a first display control unit configured to cause the display unit to display an image of the subject's eye formed on the light-receiving surface in monochrome based on an output signal from the image sensor in a case where the illumination optical system illuminates the subject's eye with the infrared light; and
   a second display control unit configured to cause the display unit to display an image of the subject's eye formed on the light-receiving surface in color based on an output signal from the image sensor in a case where the illumination optical system illuminates the subject's eye with the visible light.

14. The ophthalmologic system according to claim 13, further comprising:
   a photographing mode selection unit configured to select one of a plurality of photographing modes including a color photographing mode and an auto-fluorescence photographing mode;
   a generation unit configured to generate a display form indicating the auto-fluorescence photographing mode in a case where the photographing mode selection unit selects the auto-fluorescence photographing mode; and
   a third display control unit configured to cause the display unit to display an auto-fluorescence photographed image of the subject's eye and the display form.

15. The ophthalmologic system according to claim 13, further comprising:
   a developing unit configured to develop an output signal read from the image sensor for observation in a case where the illumination optical system illuminates the subject's eye with the infrared light,
   wherein the first display control unit causes the display unit to display a monochrome moving image of the subject's eye obtained by developing the output signal for observation.

16. The ophthalmologic system according to claim 13, further comprising:
   a removing control unit configured to remove a reflective member disposed in the camera from an optical path so that a shutter of the camera is opened in a case where the illumination optical system illuminates the subject's eye with the infrared light.

17. The ophthalmologic system according to claim 13, further comprising:
   a determination unit configured to determine a model of the camera, wherein the first or second display control unit causes the display unit to display an image in monochrome or in color based on a parameter corresponding to the determined model.

18. A recording medium recording a program for causing a computer to execute functions of the ophthalmologic system according to claim 13.

19. An ophthalmologic photographing method for an ophthalmologic photographing apparatus comprising a fundus camera body including an illumination optical system configured to illuminate a subject's eye and a photographing optical system configured to photograph the subject's eye illuminated by the illumination optical system with one of infrared light and visible light, and a camera detachable from the fundus camera body and including an image sensor with a light-receiving surface to receive return light from the subject's eye through the photographing optical system and a display unit, the ophthalmologic photographing method comprising:
   a first display control step to cause the display unit to display an image of the subject's eye formed on the light-receiving surface in monochrome based on an output signal from the image sensor in a case where the illumination optical system illuminates the subject's eye with the infrared light; and
   a second display control step configured to cause the display unit to display an image of the subject's eye formed on the light-receiving surface in color based on an output signal from the image sensor in a case where the illumination optical system illuminates the subject's eye with the visible light.

20. A recording medium recording a program for causing a computer to execute functions of the controlling method according to claim 19.

21. An ophthalmologic photographing apparatus comprising:
   an illumination optical system configured to illuminate a subject's eye;
   a photographing optical system configured to photograph the subject's eye illuminated by the illumination optical system with one of infrared light and visible light;
   an image sensor with a light-receiving surface to receive return light from the subject's eye through the photographing optical system;
   a first display control unit configured to cause the display unit to display an image of the subject's eye formed on the light-receiving surface in monochrome based on an output signal from the image sensor in a case where the illumination optical system illuminates the subject's eye with the infrared light; and
   a second display control unit configured to cause the display unit to display an auto-fluorescence photographed image of the subject's eye formed on the light-receiving surface in color based on an output signal from the image sensor in a case where the subject's eye is auto-fluorescence photographed by the illumination optical system illuminating the subject's eye with the visible light.

22. An ophthalmologic photographing apparatus comprising:
   an illumination optical system configured to illuminate a subject's eye;
   a photographing optical system configured to photograph the subject's eye illuminated by the illumination optical system with one of infrared light and visible light;
   an image sensor with a light-receiving surface to receive return light from the subject's eye through the photographing optical system;
   a display control unit configured to cause the display unit to display an image of the subject's eye formed on the light-receiving surface based on an output signal from the image sensor in a case where the illumination optical system illuminates the subject's eye with the infrared light and to cause the display unit to display an auto-fluorescence photographed image of the subject's eye formed on the light-receiving surface based on an output signal from the image sensor in a case where the subject's eye is auto-fluorescence photographed by the illumination optical system illuminating the subject's eye with the visible light.

23. The ophthalmologic photographing apparatus according to claim 22, further comprising:
a photographing mode selection unit configured to select one of a plurality of photographing modes including an auto-fluorescence photographing mode; and
a control unit configured to insert an optical filter into or remove the optical filter from at least one of the illumination optical system and the photographing optical system in a case where the auto-fluorescence photographing mode is selected by the photographing mode selection unit.

24. The ophthalmologic photographing apparatus according to claim 23, wherein the display control unit is configured to cause the display unit to display the auto-fluorescence photographed image and a display form indicating the auto-fluorescence photographing in a case where the auto-fluorescence photographing mode is selected by the photographing mode selection unit.

25. The ophthalmologic photographing apparatus according to claim 24, wherein the display control unit is configured to cause the display unit to display a display image indicating the auto-fluorescence photographing as the display form.

26. The ophthalmologic photographing apparatus according to claim 24, wherein the display control unit is configured to cause the display unit to display a character string indicating the auto-fluorescence photographing as the display form.

27. The ophthalmologic photographing apparatus according to claim 24, wherein the display control unit is configured to combine the display form with a part of the auto-fluorescence photographed image and cause the display unit to display the combined image.

28. The ophthalmologic photographing apparatus according to claim 22, further comprising:
a developing unit configured to develop an output signal read from the image sensor for observation in a case where the illumination optical system illuminates the subject's eye with the infrared light,
wherein the display control unit is configured to cause the display unit to display a monochrome moving image of the subject's eye obtained by developing the output signal for observation.

29. A method of controlling an ophthalmologic photographing apparatus including an illumination optical system configured to illuminate a subject's eye and a photographing optical system configured to photograph the subject's eye illuminated by the illumination optical system with one of infrared light and visible light, the method comprising:
causing a display unit to display an image of the subject's eye formed on a light-receiving surface of an image sensor with the light-receiving surface to receive return light from the subject's eye through the photographing optical system based on an output signal from the image sensor in a case where the illumination optical system illuminates the subject's eye with the infrared light; and
causing the display unit to display an auto-fluorescence photographed image of the subject's eye formed on the light-receiving surface based on an output signal from the image sensor in a case where the subject's eye is auto-fluorescence photographed by the illumination optical system illuminating the subject's eye with the visible light.

30. A camera attachable to a main body of a fundus camera including an illumination optical system configured to illuminate a subject's eye and a photographing optical system configured to photograph the subject's eye illuminated by the illumination optical system with one of infrared light and visible light, the camera comprising:
an image sensor with a light-receiving surface to receive return light from the subject's eye through the photographing optical system;
a display unit configured to display an image of the subject's eye formed on the light-receiving surface based on an output signal from the image sensor in a case where the illumination optical system illuminates the subject's eye with the infrared light and to display an auto-fluorescence photographed image of the subject's eye formed on the light-receiving surface based on an output signal from the image sensor in a case where the subject's eye is auto-fluorescence photographed by the illumination optical system illuminating the subject's eye with the visible light.

31. An ophthalmologic photographing system comprising:
an illumination optical system configured to illuminate a subject's eye;
a photographing optical system configured to photograph the subject's eye illuminated by the illumination optical system with one of infrared light and visible light;
an image sensor with a light-receiving surface to receive return light from the subject's eye through the photographing optical system;
a display control unit configured to cause the display unit to display an image of the subject's eye formed on the light-receiving surface based on an output signal from the image sensor in a case where the illumination optical system illuminates the subject's eye with the infrared light and to cause the display unit to display an auto-fluorescence photographed image of the subject's eye formed on the light-receiving surface based on an output signal from the image sensor in a case where the subject's eye is auto-fluorescence photographed by the illumination optical system illuminating the subject's eye with the visible light.

32. A recording medium recording a program for causing a computer to execute functions of the ophthalmologic system according to claim 31.

* * * * *